United States Patent [19]
Blewett

[11] 4,447,659
[45] May 8, 1984

[54] DECOMPOSITION OF POLYCARBONATES TO FORM TERMINALLY UNSATURATED ALCOHOLS

[75] Inventor: Charles W. Blewett, Fort Mitchell, Ky.

[73] Assignee: National Distillers and Chemical Corporation, New York, N.Y.

[21] Appl. No.: 423,897

[22] Filed: Sep. 27, 1982

[51] Int. Cl.³ .................... C07C 29/60; C07C 33/025
[52] U.S. Cl. .................................... 568/876; 260/463; 568/913
[58] Field of Search ............... 568/876, 877, 867, 866

[56] References Cited

U.S. PATENT DOCUMENTS

| 3,700,726 | 10/1972 | Johnson et al. | 568/877 |
| 3,721,714 | 3/1973 | Fenton | 568/876 |
| 4,217,297 | 8/1980 | Lindner et al. | 260/463 |
| 4,267,303 | 5/1981 | Konig et al. | 260/463 |

Primary Examiner—J. E. Evans
Attorney, Agent, or Firm—Kenneth D. Tremain; Gerald A. Baracka

[57] ABSTRACT

Process for the preparation of terminally unsaturated alcohols by the thermal decomposition of a polycarbonate in the presence of titanium containing catalyst.

13 Claims, No Drawings

DECOMPOSITION OF POLYCARBONATES TO FORM TERMINALLY UNSATURATED ALCOHOLS

BACKGROUND OF THE INVENTION

This invention relates to a process for preparing unsaturated alcohols and more particularly to a process for the preparation of terminally unsaturated alcohols from diols.

Unsaturated aliphatic alcohols are well-known commodities, having varied utilities, and are prepared by a variety of techniques.

For example, U.S. Pat. No. 2,086,713 to Grun describes a process of producing olefin alcohols by mixing dihydroxy alcohols in the liquid phase with a catalyst selected from the group consisting of hydroxides of aluminum, zirconium, titanium and thorium and heating the mixture to temperature above the boiling point of water.

U.S. Pat. No. 3,862,964 to Weisang et al. discloses a catalyst for dehydrating diols which consists of one mixed or unmixed pyrophosphate of at least one metal chosen from the group consisting of lithium, sodium, strontium and barium, and a compound of chromium chosen from the group consisting of chromium oxide and chromium phosphate in an amount less than about 2% of the total weight of the catalyst. To the same effect is U.S. Pat. No. 3,957,900, also of Weisang et al., which describes a specific method of dehydration including contacting the diol in the vapor phase in the presence of inert gas with a mechanically strengthened catalyst formed by calcining a mass formed by mixing finely divided solid particles of at least one pyrophosphate and one acid orthophosphate of a metal belonging to the group consisting of lithium, sodium, strontium and barium.

U.S. Pat. No. 3,670,032 to Romanelli describes the preparation of unsaturated alcohols and ethers through the reaction of $C_4$ to $C_6$ aliphatic conjugated diolefins with water, a lower alkanol in the presence of a zero valent palladium based catalyst system, e.g., triphenylphosphine palladium, and a basic cocatalyst selected from the group consisting of tetraalkyl and trialkylaralkyl ammonium hydroxide and alkoxides having 4 to 20 carbon atoms, at a temperature between 0° and 125° C.

U.S. Pat. No. 2,454,936 to Morey discloses a process for preparation of aliphatic unsaturated monohydric alcohols by adding water, not in excess of 10 percent by total weight, to an aliphatic dihydric alcohol having the following structural formula:

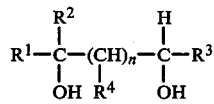

in which $R^1$ and $R^2$ are alkyl radicals, $R^3$ and $R^4$ are one of hydrogen and alkyl radicals, and n is an integer from 1 to 4, and adding thereto a dehydration catalyst selected from the group consisting of p-toluenesulfonic acid, iodine, aniline hydroiodide and hydrogen iodide. The mixture is rapidly distilled and condensed yielding an oil condensate containing isomeric monomeric monohydric unsaturated alcohols.

U.S. Pat. No. 2,583,426 to Hillyer, et al. relates to the production of unsaturated primary alcohols containing five or more carbon atoms which comprises contacting an epoxy compound having olefinic unsaturation with a Grignard reagent.

U.S. Pat. No. 3,721,714 to Fenton describes a process for preparing aldehydes and alcohols by contacting a dicarbohydryl carbonate with a catalyst comprised of a complex of a Group VIII noble metal and a biphyllic ligand (e.g. to triphenylphosphine) at a temperature between 150° C. and 250° C. Similarly, U.S. Pat. No. 3,784,616 to Fenton shows a process for the preparation of aldehydes and alcohols by contacting dihydrocarbyl oxalate with a catalyst comprising a Group VIII noble metal and biphyllic ligand at a temperature between 150° C. and 250° C. and at a pressure sufficient to maintain liquid phase reaction.

J. W. Hill and W. H. Carothers, *J. Am. Chem. Soc.*, 55, 5031(1933) disclose a process for the preparation of cyclic ester products by depolymerization of polyesters. It is also disclosed therein, that 9-decen-1-ol is a by-product from the sodium methoxide catalyzed depolymerization of polymeric decamethylene carbonate. The yield of 9-decen-1-ol is only about 2 percent wherein the principal products of the reaction are the cyclic carbonate and cyclic dicarbonate.

Moreover, Searles et al., *J. Am. Chem. Soc.*, 82, 2928(1960), disclose a process for the formation of terminally unsaturated alcohols by the pyrolysis of cyclic carbonates in the presence of a basic catalyst such as potassium cyanide (KCN), while Williams et al. J.O.C. 23, 676 (1958) disclose the formation of terminally unsaturated alcohols from carbonates in the absence of a catalyst. These processes are not totally satisfactory because of the low yields obtained and, in the case of Williams et al., the high temperatures (500° C.) required to achieve pyrolysis.

Thus, while the art is cognizant of many procedures for the preparation of unsaturated alcohols, other simpler, less cumbersome, more economic processes producing high yields of valuable product are very desirable.

SUMMARY OF THE INVENTION

Accordingly, it is one object of the present invention to provide a novel process for the preparation of terminally unsaturated alcohols.

It is another object of this invention to provide an efficient, inexpensive method for the production of terminally unsaturated alcohols.

These and other objects are achieved herein by a process which comprises thermally decomposing a polycarbonate in the presence of a titanium containing catalyst. In one embodiment of the invention, a diol is contacted with a dialkyl carbonate in the presence of a titanium containing catalyst to form a polycarbonate and the resulting polycarbonate then decomposed in the presence of the titanium catalyst to obtain a terminally unsaturated alcohol.

DETAILED DESCRIPTION OF THE INVENTION

In general, and in one embodiment herein, the process of the present invention comprises first reacting a diol with a dialkyl carbonate, in the presence of a titanium catalyst, to form a polycarbonate. The temperature of the reaction is then increased in order to thermally decompose the polycarbonate to obtain the unsaturated alcohol.

Accordingly, the process of this invention can be represented by the following reaction scheme:

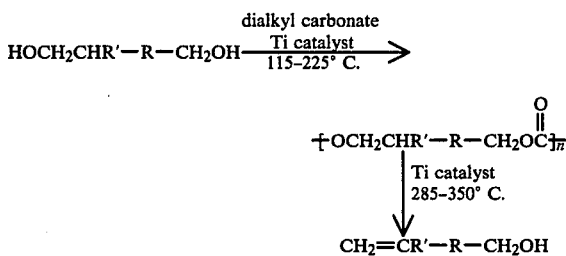

wherein R is a bivalent aliphatic (alkylene) radical having from about 3 to 19 carbon atoms and R' is hydrogen or an alkyl group. R and R' can be straight-chained or branched. Typically R can be propylene, butylene, hexylene, nonylene, etc. The dialkyl carbonate reactant can have from 3 to 9 carbon atoms and n is an integer which can vary over a wide range, such as, for example, from about 2 to about 400 and more preferably from about 5 to about 100.

Typical diols which are reacted with the dialkyl carbonate herein include diols having from 6 to 22 carbon atoms and correspond to the formula $HOCH_2CHR'—R—CH_2OH$ wherein R and R' are the same as defined above. Illustrative diols include hexanediols, decanediols, dodecanediols, nonanediols, eiconsanediols, and the like. Preferred diols for the purposes of this invention have from about 8 to about 14 carbon atoms.

Dialkyl carbonates within the scope of the present process include for example, dimethyl carbonate, diethyl carbonate, dipropyl carbonate, dibutyl carbonate, ethylene carbonate and the like.

A titanium catalyst is preferably utilized in both steps of the reaction of the present invention. Suitable catalysts employed in the present process include titanates of the formula $Ti(OR'')_4$, and condensates thereof, wherein R'' is, for example, a $C_1$-$C_{10}$ alkyl group, titanium chelates, titanium acylates and the like.

More specifically, typical titanates utilized as a catalyst herein include, for example, $Ti(OC_3H_7)_4$ (tetraisopropyl titanate), $Ti(OC_4H_9)_4$ (tetrakis(2-ethylhexy)titanate) and the like. Typical titanium chelates, include, for example, titanium acetylacetonate, lactic acid titanium chelates, triethanolamine titanium chelate, titanium ethylacetoacetate chelate, tetraoctylene glycol titanate and the like. Representative titanium acylates include, for example, those of the formula $Ti(OCOR'')_4$, wherein R'' is as hereinbefore defined. Many, if not all, of the aforedescribed titanium catalysts are available from the Dupont Chemical Company under the trademark "Tyzor".

The polycarbonate preparation stage is generally preformed at relatively low temperatures, e.g. 100°-225° C. and preferably from about 115° C. to about 200° C., and at pressure from about 0.5 to about 2 atmospheres, preferably at 1 atmosphere.

In the second stage of the present process, i.e. decomposition of the polycarbonate, in general the polycarbonate and catalyst are heated to the decomposition temperature of the polycarbonate at atmospheric pressure or subjected to stripping under vacuum conditions and then heated to the final reaction temperature. The titanium catalysts utilized in the decomposition step are the same as described hereinbefore. Moreover, the titanium catalyst used in the decomposition step may be the same or different from that used in the polycarbonate formation step. The distillate that is formed is collected and the reaction is continued until no further distillate is recovered.

While one embodiment of the present invention involves the initial preparation of the polycarbonates as hereinbefore illustrated, it is also within the scope of the present invention to thermally decompose polycarbonates derived from any source (e.g. as prepared herein or from any other synthetic route or obtained commercially) in the presence of the afore-described titanium catalysts and reaction conditions to provide excellent yields of terminally unsaturated alcohol.

The amount of titanium catalyst which is employed in the reactions of the present invention can vary widely. For example, suitable amounts for the purposes of this invention are from about 0.5 to 10 weight percent; preferably from about 0.75 weight percent to about 4 weight percent. These ranges are applicable to the situation where the titanium catalyst is used herein for the preparation of the polycarbonate by reaction of a diol and dialkyl carbonate, in which event the weight percent is based on the diol, or the situation where preformed polycarbonate is decomposed, in which case the weight percent is based on the polycarbonate.

Purification of the recovered terminally unsaturated alcohols can be effected by conventional distillation since the other components present in the crude distillate, the alpha, omega-diene and the diol, are of much higher and much lower volatility than the terminally unsaturated alcohol.

Thus, in accordance with the present process, which utilizes a titanium catalyst in the polycarbonate formation, and/or in the subsequent polycarbonate decomposition, increased yields e.g. in the 60–65% range, of product are obtained. The terminally unsaturated alcohols generated in accordance with the process of the present invention have utility as fragrance components and as intermediates for the synthesis of insect sex attactants. For example, terminally unsaturated alcohols prepared in accordance with this invention include 7-octen-1-ol, 8-nonen-1-ol, 9-decen-1-ol, 11-dodecen-1-ol, 19-eicosen-1-ol, and the like.

The following examples are given by way of illustration and not by way of limitation in order that those skilled in the art may better understand how to practice the present invention.

EXAMPLE 1

1,10-Decanediol (175 grams) and 167 grams diethyl carbonate are charged to a reactor equipped with a Claisen head for distillation. The reaction mixture is heated to approximately 140° C. and sufficient diethyl carbonate (about 25 grams) distilled off to remove any traces of water present in the reaction mixture. After cooling to 110° C., 2.5 cc tetraisopropyl titanate (TIP) (about 1.5 wt. percent based on the diol) is added and the temperature slowly increased. Ethanol begins distilling at about 115°–120° C. When the temperature reaches 225° C., the reaction mixture is stripped for about one hour under water aspirator vacuum to remove any unreacted diethyl carbonate from the poly(decamethylene carbonate).

The resulting polycarbonate is then decomposed by heating to 310° C. under aspirator vacuum (25–30 mm Hg) while removing distillate. Evolution of $CO_2$ is observed. Heating is continued until no further distillate is recovered. Gas chromatographic analysis of the crude distillate shows it to contain about 75 wt. percent 9-decen-1-ol. The reaction gives 93.7% conversion, based on the 1,10-decanediol, with 65.7% selectivity to the desired 9-decen-1-ol. Final purification to obtain pure 9-decen-1-ol is effected by vacuum distillation. (boiling pont 234°–238° C.; $n_D^{20}$ 1.4480; d 0.876). The structure of the 9-decen-1-ol is confirmed by gas chromatography/mass spectroscopy.

EXAMPLE 2

1,10-Decanediol (175 grams) and 167 grams diethyl carbonate are charged to a reactor equipped with a Claisen head for distillation. The reaction mixture is heated to approximately 140° C. and sufficient diethyl carbonate (about 25 grams) distilled off to remove any traces of water present in the reaction mixture. After cooling to 110° C., 2.5 cc titanium acetylacetonate (Tyzor®AA) (about 1.5 wt. percent based on the diol) is added and the temperature slowly increased. Ethanol begins distilling at about 115°–120° C. When the temperature reaches 225° C., the reaction mixture is stripped for about one hour under water aspirator vacuum to remove any unreacted diethyl carbonate from the poly(decamethylene carbonate).

The resulting polycarbonate is then decomposed by heating to 310° C. under aspirator vacuum (25–30 mm Hg) while removing distillate. Evolution of $CO_2$ is observed. Heating is continued until no further distillate is recovered. Gas chromatographic analysis of the crude distillate shows it to contain about 73.6 wt. percent 9-decen-1-ol. The reaction gives 94% conversion, based on the 1,10-decanediol, with 75.5% selectivity to the desired 9-decen-1-ol. Final purification to obtain pure 9-decen-1-ol is effected by vacuum distillation. (boiling point 234°–238° C.; $n_D^{20}$ 1.4480; d 0.876). The structure of the 9-decen-1-ol is confirmed by gas chromatography/mass spectroscopy.

EXAMPLE 3

1,10-Decanediol (175 grams) and 167 grams diethyl carbonate are charged to a reactor equipped with a Claisen head for distillation. The reaction mixture is heated to approximately 140° C. and sufficient diethyl carbonate (about 25 grams) distilled off to remove any traces of water present in the reaction mixture. After cooling to 110° C., 2.5 cc tetrakis(2-ethylhexyl) titanate (Tyzor®TOT) (about 1.5 wt. percent based on the diol) is added and the temperature slowly increased. Ethanol begins distilling at about 115°–120° C. When the temperature reaches 225° C. the reaction mixture is stripped for about one hour under water aspirator vacuum to remove any unreacted diethyl carbonate from the poly(decamethylene carbonate).

The resulting polycarbonate is then decomposed by heating to 310° C. under aspirator vacuum (25–30 mm Hg) while removing distillate. Evolution of $CO_2$ is observed. Heating is continued until no further distillate is recovered. Gas chromatographic analysis of the crude distillate shows it to contain about 76.4 wt. percent 9-decen-1-ol. The reaction gives 93.9% conversion, based on the 1,10-decanediol, with 74.1% selectivity to the desired 9-decen-1-ol. Final purification to obtain pure 9-decen-1-ol is effected by vacuum distillation. (boiling point 234°–238° C.; $n_D^{20}$ 1.4480; d 0.876). The structure of the 9-decen-1-ol is confirmed by gas chromatography/mass spectroscopy.

EXAMPLE 4

1,10-Decanediol (175 grams) and 167 grams diethyl carbonate are charged to a reactor equipped with a Claisen head for distillation. The reaction mixture is heated to approximately 140° C. and sufficient diethyl carbonate (about 25 grams) distilled off to remove any traces of water present in the reaction mixture. After cooling to 110° C., 2.5 cc tetraoctylene glycol titanate (Tyzor®OG) (about 1.5 wt. percent based on the diol), is added and the temperature slowly increased. Ethanol begins distilled at about 115°–120° C. When the temperature reaches 225° C., the reaction mixture is stripped for about one hour under water aspirator vacuum to remove any unreacted diethyl carbonate from the poly(decamethylene carbonate).

The resulting polycarbonate is then decomposed by heating to 310° C. under aspirator vacuum (25–30 mm Hg) while removing distillate. Evolution of $CO_2$ is observed. Heating is continued until no further distillate is recovered. Gas chromatographic analysis of the crude distillate shows it to contain about 74.1 wt. percent 9-decen-1-ol. The reaction gives 92.6% conversion, based on the 1,10-decanediol, with 75.6% selectivity to the desired 9-decen-1-ol. Final purification to obtain pure 9-decen-1-ol is effected by vacuum distillation. (boiling point 234°–238° C.; $n_D^{20}$ 1.4480; d 0.876). The structure of the 9-decen-1-ol is confirmed by gas chromatography/mass spectroscopy.

EXAMPLE 5

A mixture weighing 68.7 g of 1,20-eicosanediol with its mono- and dipivalate esters having the following composition is combined with 56 g of diethyl carbonate:

$C_{20}$ Diol: 47.0%
$C_{20}$ Diol monopivalate ester: 30.6%
$C_{20}$ Diol dipivalate esters: 16.0%
Unknowns: 6.4%

The reaction mixture is heated in an apparatus set for distillation through a Claisen head until 25 ml of diethyl carbonate is distilled off. The reaction mixture is then cooled to 100° C. and 1.7 ml titanium acetylacetonate (Tyzor®AA (DuPont)) is added. The reaction mixture is reheated to 130° C. and distillation begins. The reaction mixture is kept at 130° C. until no further distillate comes off, then heated slowly to 225° C. The reaction mixture is then held at 25 mm Hg pressure for 45 minutes. The reaction mixture is then heated to 310° C. under 5–10 mm Hg pressure. Heavy white smoke is evident, and a white solid condensate forms on the condenser, receiver flask, and in vacuum lines. The reaction mixture is cooled to 200° C., to clear the vacuum lines and the system is then reheated to 310° C. Heavy smoke and white solid condensate are again formed with blockage of the lines. The cooling and reheating are repeated several times, and eventually 36.4 g of distillate is obtained. Gas chromatographic analysis of the crude distillate shows it to contain about 67.7 wt.% 19-eicosen-1-ol. The reaction gives 92.1% conversion with 50.7 percent selectivity.

EXAMPLES 6–13

Several processes are conducted in accordance with the general procedure described in Example 1. For these examples various diols are employed and the amount of tetraisopropyl titanate (TIP) catalyst is varied. Details of the experiments and the results obtained are provided in Table 1. Percent conversion reported in the table is based on the diol and percent selectivity is to the corresponding alpha, omega-ene/ol.

TABLE 1

| Example | Diol (g) | Weight Percent Catalyst | Mole % Diethyl carbonate | % Conversion | % Selectivity |
|---|---|---|---|---|---|
| 6 | C$_6$(113) | 1.3 | 120 | 96.3 | 68.1 |
| 7 | C$_8$(211) | 1.5 | 120 | 96.3 | 73.7 |
| 8 | C$_9$(190) | 1.5 | 120 | 90.5 | 73.6 |
| 9 | C$_{12}$(324) | 1.3 | 120 | 95.2 | 72.7 |
| 10 | C$_{10}$(351) | 0.94 | 120 | 95.4 | 70.7 |
| 11 | C$_{10}$(351) | 1.42 | 120 | 94.0 | 73.9 |
| 12 | C$_{10}$(351) | 1.88 | 120 | 94.1 | 75.4 |
| 13 | C$_{10}$(265) | 3.70 | 120 | 96.4 | 72.7 |

EXAMPLES 14-17

Following the general procedure described in Example 1 experiments were carried out using different polycarbonate decomposition temperatures. The type and amount of reactant and catalyst were also varied and are reported in Table 2 with the results for these reactions. Percent conversion reported in the table is based on the diol and percent selectivity is to the corresponding alpha, omega-ene/ol.

TABLE 2

| Example | Diol (g) | Catalyst (wt. %) | Mole % Diethyl carbonate | Decomposition Temp. (°C.) | % Conversion | % Selectivity |
|---|---|---|---|---|---|---|
| 14 | 6(107.0) | TIP(1.4) | 165 | 300 | 99.4 | 66.6 |
| 15 | 6(113.3) | TIP(1.3) | 120 | 310 | 96.3 | 68.0 |
| 16 | 6(113.6) | TIP(1.3) | 120 | 320 | 96.2 | 72.4 |
| 17 | 10(167.0) | Tyzor ® AA(2.5) | 120 | 340 | 93.7 | 71.5 |

Obviously, other modifications and variations of the present invention are possible in the light of the above teaching. It is, therefore, to be understood that changes may be made in the particular embodiments of this invention which are within the full intended scope of the invention as defined by the appended claims.

What is claimed is:

1. A process for the preparation of terminally unsaturated alcohols, said process comprising thermally decomposing a polycarbonate represented by the formula:

wherein R is a bivalent alkylene radical having from 3 to about 19 carbon atoms, R$^1$ is hydrogen or an alkyl group and n is an integer from about 2 to about 500 in the presence of a titanium containing catalyst selected from the group consisting of titanates, condensates of said titanates, titanium chelates and titanium acylates.

2. The process of claim 1 wherein said titanium catalyst is selected from the group consisting of tetraisopropyltitanate, tetra-n-butyltitanate, tetrakis (2-ethylhexyltitinate), titanium acetylacetonate, lactic acid titanium chelate, triethanolamine titanium chelate, titanium ethylacetoacetate chelate, tetraoctylene glycol titanate and titanium acylates of the formula Ti(OCOR")$_4$ wherein R" is a C$_1$-C$_{10}$ alkyl group.

3. The process of claim 1 wherein the thermal decomposition is carried out at a temperature in the range of from about 285° C. to about 350° C.

4. The process of claim 1 wherein said titanium catalyst is tetraisopropyltitanate.

5. A process for the preparation of terminally unsaturated alcohols, said process comprising the steps of:
(i) contacting a diol with a dialkyl carbonate in the presence of a titanium containing catalyst to form a polycarbonate; and
(ii) thermally decomposing the polycarbonate formed in step (i) in the presence of a titanium containing catalyst wherein said titanium catalyst in steps (i) and (ii) is independently selected from the group consisting of titanates, condensates of said titanates, titanium chelates and titanium acylates.

6. The process of claim 5 wherein said diol is represented by the formula:

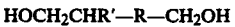

wherein R is a bivalent alkylene radical having from 3 to about 19 carbon atoms and R' is hydrogen or an alkyl group.

7. The process of claim 5 wherein the dialkyl carbonate contains from 3 to about 9 carbon atoms.

8. The process of claim 5 wherein said titanium catalyst in steps (i) and (ii) is selected from the group consisting of tetraisopropyltitanate, tetra-n-butyltitanate, tetrakis (2-ethylhexytitanate), titanium acetylacetonate, lactic acid titanium chelate, triethanolamine titanium chelate, titanium ethylacetoacetate chelate, tetraoctylene glycol titanate and titanium acylates of the formula Ti(OCOR")$_4$ wherein R" is a C$_1$-C$_{10}$ alkyl group.

9. The process of claim 5 wherein step (i) is carried out at a temperature in the range of from about 115° C. to about 225° C. and step (ii) is carried out at a temperature in the range of from about 285° C. to about 350° C.

10. The process of claim 5 wherein said diol is selected from the group consisting of 1,6-hexanediol, 1,10-decanediol, 1,8-octanediol, 1,9-nonanediol, 1,12-dodecanediol, 1,20-eicosanediol and mixtures thereof, and the dialkyl carbonate is selected from the group consisting of dimethyl carbonate, diethyl carbonate, dipropyl carbonate, dibutyl carbonate and ethylene carbonate.

11. The process of claim 10 wherein said titanium catalyst in steps (i) and (ii) is tetraisopropyltitanate.

12. The process of claim 1 wherein the resulting terminally unsaturated alcohol is continuously removed from the reaction mixture during the decomposition of said polycarbonate.

13. The process of claim 5 wherein the resulting terminally unsaturated alcohol is continuously removed from the reaction mixture during the decomposition of said polycarbonate.

* * * * *